US00PP15553P2

(12) United States Plant Patent
Zaiger et al.

(10) Patent No.: US PP15,553 P2
(45) Date of Patent: Feb. 8, 2005

(54) PLUM TREE NAMED 'HOLIDAY'

(50) Latin Name: *Prunus salicina*
Varietal Denomination: Holiday

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/747,518

(22) Filed: Dec. 30, 2003

(51) Int. Cl.[7] ..... A01H 5/00
(52) U.S. Cl. ..... Plt./184
(58) Field of Search ..... Plt./184

*Primary Examiner*—Anne Marie Grunberg

(57) ABSTRACT

A new and distinct variety of plum tree (*Prunus salicina*). The following features of the tree and its fruit are characterized with the tree budded on 'Nemagaurd' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features:

1. Fruit ripening in the late maturity season.
2. Fruit holding firm on the tree 2 weeks after maturity (shipping ripe).
3. Fruit with a high Brix of 18.7°.
4. Fruit with very good storage.
5. Heavy and regular production of fruit.
6. Fruit with relatively uniform large size fruit throughout the tree.

1 Drawing Sheet

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of plum tree was originated and asexually reproduced by us in our experimental orchard located near Modesto, Stanislaus County, Calif.

2. Prior Varieties

Among the existing varieties of plum trees, which are known to us, and mentioned herein, 'Friar' Plum (non-patented), 'King David' Plum (non-patented) and 'Autumn Pride' Plum (U.S. Plant Pat. No. 7,843).

STATEMENT REGARDING FEDERALLY SPONSORED RESEARCH AND DEVELOPMENT

Not applicable.

ORIGIN OF THE VARIETY

The new and distinct variety of plum tree (*Prunus salicina*) was originated by us in our experimental orchard, located near Modesto, Calif., as a first generation cross between a proprietary parent with the field identification number 46ED305 and 'Autumn Pride' (U.S. Plant Pat. No. 7,843). The maternal parent (46ED305) originated from a second generation seedling of open pollinated seed from 'King David' Plum (non-patented). We planted and maintained a large number of these first generation seedlings, growing on their own root system, under close observation, during which time one seedling exhibited desirable, late maturing fruit characteristics and was selected in 1991 for asexual propagation and commercialization.

ASEXUAL REPRODUCTION OF THE VARIETY

Asexual reproduction of the new and distinct variety of plum tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of plum tree (*Prunus salicina*) is of large size, vigorous, upright growth and a regular bearer of large, yellow flesh, clingstone fruit with a sweet tart flavor and good eating quality. The fruit is further characterized by having moderately juicy, firm flesh, maturing in the late maturity season, excellent storage, good shipping quality and holding firm on the tree for 2 weeks after shipping ripe. In comparison to the late maturing 'Autumn Pride' Plum (U.S. Plant Pat. No. 7,843), the variety that it most closely resembles, the fruit of the new variety is larger in size, has green-yellow skin color compared to a reddish purple, is more elongated in shape and is approximately 30 days later in maturity.

PHOTOGRAPH OF THE VARIETY

The accompanying color photographic illustration shows typical specimens of the foliage and fruit of the present new plum variety. The illustration shows the upper and lower surface of the leaves, an exterior and sectional view of a fruit divided in its suture plane to show flesh color, pit cavity and the stone remaining in place.

The photographic illustration was taken shortly after being picked (shipping ripe) and the colors are as nearly true as is reasonably possible in a color representation of this type.

DESCRIPTION OF THE VARIETY

The following is a detailed botanical description of the new variety of plum tree, its flowers, foliage and fruit, as based on observations of 8 year old specimens grown near Modesto, Calif., with color in accordance with Munsell Book of Color.

Tree:

*Size*.—Large. Pruned 3 to 3.5 meters in height primarily for economical harvesting of fruit.

*Vigor*.—Vigorous, growth of 1.5 to 2 meters in the first growing season. Varies with fertility, type of soil and climatic conditions.

*Form*.—Upright, becomes more spreading with crop load.

*Branching habit*.—Upright, crotch angle approximately 30°, increases with heavy crop load.

*Productivity*.—Productive, usually sets 1 to 1½ times more fruit than desired, thinning and spacing of fruit necessary.

*Bearer*.—Regular. Adequate fruit set 5 consecutive years. No alternate bearing observed.

*Fertility*.—Self sterile, pollenizer required.

*Density*.—Medium dense. Usually pruned to vase shape to allow more sunlight and air movement in center of tree to enhance Brix and health of fruit spurs.

*Hardiness*.—Hardy in all stone fruit growing areas of California. Winter chilling requirement approximately 650 to 700 hours at or below 45° F.

Trunk:

*Size*.—Medium to large. Average circumference 55.7 cm at 30.5 cm above ground on 8 year old tree.

*Stocky*.—Medium stocky.

*Texture*.—Medium shaggy.

*Color*.—Varies from 7.5YR 6/2 to 10YR 6/2.

Branches:

*Size*.—Medium size. Average circumference 16.0 cm at 1.5 meters above ground.

*Surface texture*.—New growth smooth, old growth medium rough, becoming rougher with age.

*Lenticels*.—Average number 26 in a 25.8 square cm section. Average length 6.4 mm. Average width 1.3 mm. Color varies from 5YR 6/6 to 5YR 5/10.

*Color*.—New growth varies from 2.5GY 6/6 to 7.5YR 6/6. Old growth varies from 5YR 3/4 to 7.5YR 3/4.

Leaves:

*Size*.—Small to medium. Average length 106.0 mm. Average width 41.0 mm.

*Form*.—Oblanceolate.

*Apex*.—Acuminate.

*Base*.—Cuneate.

*Margin*.—Doubly serrate.

*Thickness*.—Medium, average for plums.

*Surface texture*.—Upper surface relatively smooth, slight indentations over midrib and leaf veins, glabrous. Lower surface relatively smooth, except for small ridges created by midrib and pinnate venation, glabrous.

*Petiole*.—Average length 10.5 mm. Average width 1.6 mm. Color varies from 2.5GY 7/6 to 7.5R 7/10. Varies with exposure to sunlight. Surface — glabrous.

*Glands*.—Globose. Size — small. Average length 0.7 mm. Average width 0.4 mm. Number varies from 2 to 4, average number 3. Located on base of leaf blade and upper portion of petiole. Color varies from 2.5GY 6/6 to 5GY 6/6.

*Color*.—Upper surface varies from 5GY 3/4 to 5GY 3/6. Lower surface varies from 5GY 5/4 to 5GY 4/4. Midvein color varies from 2.5GY 7/4 to 5GY 8/4.

Flower buds:

*Size*.—Medium. Average length 8.7 mm. Average diameter 4.9 mm.

*Hardiness*.—Hardy in all stone fruit growing areas of California.

*Form*.—Conical, becoming elongated before opening.

*Pedicel*.—Average length 13.1 mm. Average width 1.1 mm. Color 2.5GY 7/6.

*Color*.—N 9.5/.

*Number of buds per spur*.—Varies from 2 to 10, average 7.

Flowers:

*Size*.—Medium. Average height 11.5 mm. Average diameter 16.4 mm.

*Petals*.—Usually 5, alternately arranged to sepals. Shape — ovate, narrows at point of attachment. Average length 9.6 mm. Average width 7.5 mm. Margin — entire, slightly cupped near apex.

*Sepals*.—Usually 5, alternately arranged to petals. Shape — triangular. Both upper and lower surfaces glabrous. Average length 3.6 mm. Average width 2.3 mm. Color — upper surface 5GY 7/8, lower surface 5GY 6/8.

*Stamens*.—Average number per flower 30. Average filament length 6.4 mm. Filament color N 9.5/. Anther color 10R 6/10.

*Pollen*.—Self sterile, pollenizer required. Color 7.5YR 7/10.

*Pistil*.—Number — usually one, varies from 1 to 2. Average length 8.7 mm. Color 2.5GY 9/4. Surface — glabrous. Height compared to stamens approximately 1.0 mm lower.

*Fragrance*.—Slight aroma.

*Blooming period*.—Date of First Bloom Feb. 25, 2003. Date of Petal Fall Mar. 5, 2003. Varies slightly with climatic conditions.

*Color*.—N 9.5/.

*Number flowers per flower bud*.—Usually 2, varies from 1 to 3.

*Pedicel*.—Average length 13.3 mm. Average width 1.3 mm. Color varies from 2.5GY 7/6 to 2.5GY 7/8.

Fruit:

*Maturity when described*.—Firm ripe.

*Date of first picking*.—Oct. 23, 2003.

*Date of last picking*.—Oct. 29, 2003. Varies slightly with climatic conditions.

*Size*.—Large. Average diameter axially 73.6 mm. Average transversely in suture plane 67.2 mm. Average weight 201.6 grams. Average weight varies slightly with fertility of the soil, amount of thinning and climatic conditions.

*Form*.—Cordite, heart shape.

*Suture*.—Shallow, nearly smooth.

*Ventral surface*.—Nearly smooth, extends from base to apex.

*Apex*.—Varies from slight point to nearly rounded.

*Base*.—Flat.
*Cavity*.—Rounded to slightly elongated in suture plane. Average depth 2.5 mm. Average diameter 10.0 mm.

Stem:
*Size*.—Medium. Average length 14.2 mm. Average width 2.1 mm.
*Color*.—Varies from 2.5YR 3/8 to 5YR 3/6.

Flesh:
*Ripens*.—Evenly.
*Texture*.—Firm, meaty.
*Fibers*.—Few, small, tender.
*Firmness*.—Firm, smooth, comparable to 'Friar' Plum (non-patented).
*Aroma*.—Very slight.
*Amydgalin*.—None.
*Eating quality*.—Good.
*Flavor*.—Good, slightly tart near skin.
*Juice*.—Moderate.
*Brix*.—Average 18.7°, varies slightly with amount of fruit per tree and climatic conditions.
*Color*.—Varies from 2.5Y 8.5/6 to 2.5Y 8/8. Pit color varies from 10YR 7/8 to 10YR 6/10, no bleeding into flesh.

Skin:
*Thickness*.—Medium.
*Surface*.—Smooth.
*Bloom*.—Moderate, complete coverage.
*Tendency to crack*.—Very slight.
*Color*.—Color varies from 5Y 7/8 to 10Y 7/6.
*Tenacity*.—Tenacious to flesh.
*Astringency*.—None.

Stone:
*Type*.—Clingstone.
*Size*.—Large. Average length 29.8 mm. Average width 22.6 mm. Average thickness 13.0 mm.
*Form*.—Ovate.
*Base*.—Usually flat, some stones slightly concaved.
*Apex*.—Cuspidate, small. Average length 1.8 mm.
*Surface*.—Very lightly pitted throughout, one small groove on each side of suture.
*Sides*.—Unequal, with one side extending further from the suture plane.
*Ridges*.—Small, narrow ridges extending a short distance from base toward apex.
*Tendency to split*.—None.
*Color*.—Varies from 10YR 8/8 to 10YR 7/8 when dry.

Kernal:
*Form*.—Ovate.
*Taste*.—Bitter.
*Viability*.—Viable, complete embryo.
*Size*.—Medium. Average length 16.2 mm. Average width 10.8 mm. Average thickness 5.8 mm.
*Skin color*.—Varies from 10YR 5/8 to 10YR 7/8 when dry.

Use: Dessert. Market — local and long distance.

Keeping quality: Very good, held firm 30 days in cold storage at 38° to 42° without internal breakdown in flesh, with slight loss of acidity, flavor and eating quality good.

Shipping quality: Good, picking, packing and shipping gave minimal scarring of skin or flesh bruising during shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance of susceptibility has been observed. Any variety observed during indexing of plant characteristics with abnormal fungus, bacterial, virus or insect susceptibility is destroyed and eliminated from our breeding program.

The present new variety of plum tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of plum tree, substantially as illustrated and described, characterized by its large size, vigorous, upright growth and being a productive and regular bearer of large, late maturing, yellow flesh, clingstone fruit with good flavor and eating quality; the fruit is further characterized by having firm flesh, holding firm on tree 2 weeks after maturity (shipping ripe), having very good storage and good shipping quality and in comparison to the late maturing 'Autumn Pride' Plum (U.S. Plant Pat. No. 7,843), the new variety is larger in size and is approximately 30 days later in maturity.

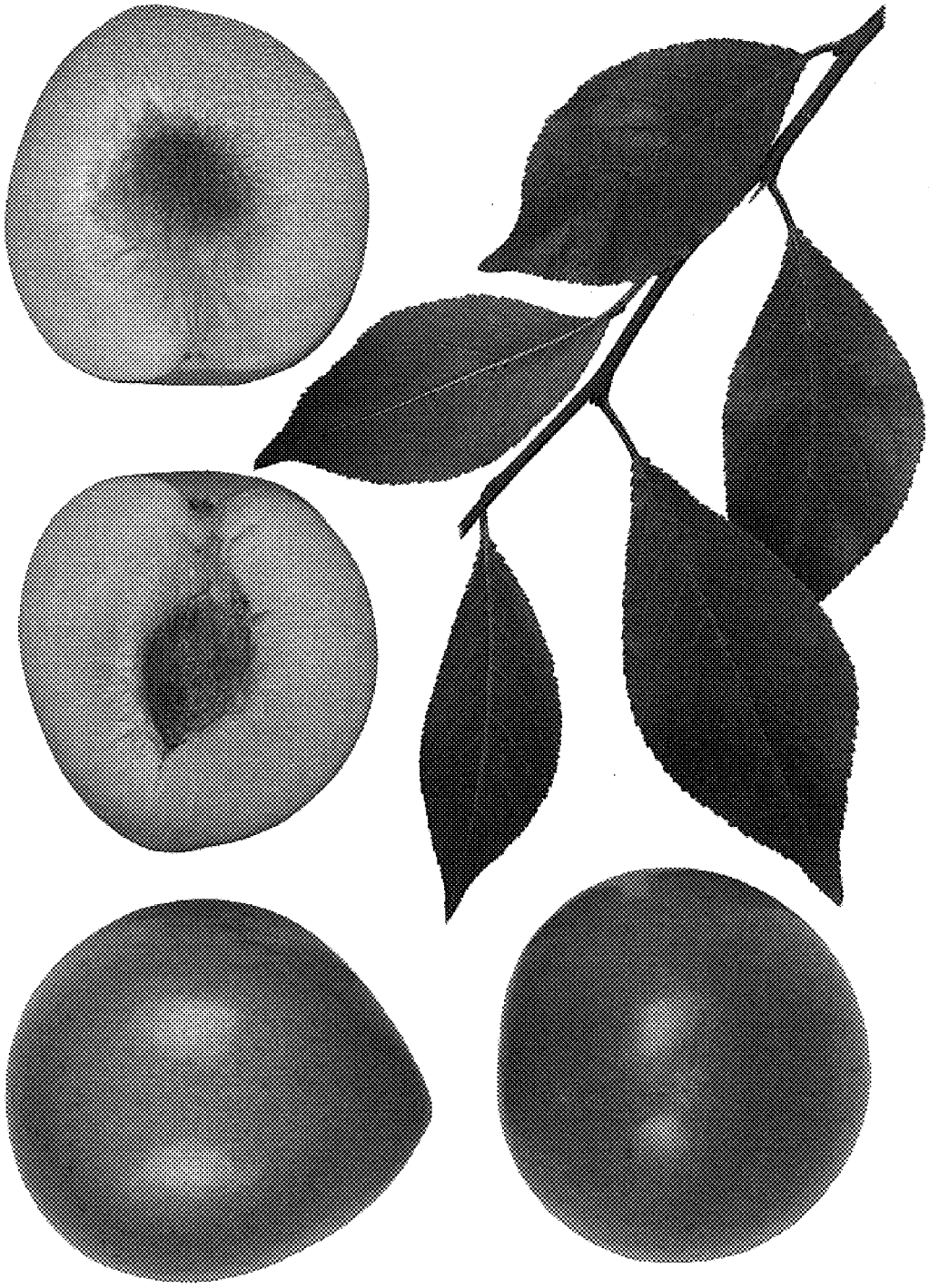

* * * * *